US006462218B1

United States Patent
Hallenbach et al.

(10) Patent No.: US 6,462,218 B1
(45) Date of Patent: Oct. 8, 2002

(54) METHOD FOR PREPARING 3-CYANO-2,4-DIHALOGENO-5-FLUORO-BENZOIC ACID

(75) Inventors: Werner Hallenbach, Monheim; Albrecht Marhold, Leverkusen, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/463,272

(22) PCT Filed: Jul. 18, 1998

(86) PCT No.: PCT/EP98/04468

§ 371 (c)(1),
(2), (4) Date: Jan. 24, 2000

(87) PCT Pub. No.: WO99/06360

PCT Pub. Date: Feb. 11, 1999

(30) Foreign Application Priority Data

Aug. 1, 1997 (DE) .......................................... 197 33 243

(51) Int. Cl.[7] ............................................. C07C 255/51
(52) U.S. Cl. ........................................ 558/425; 558/406
(58) Field of Search .................................. 558/425, 406

(56) References Cited

U.S. PATENT DOCUMENTS

| | | |
|---|---|---|
| 4,908,366 | 3/1990 | Schriewer et al. |
| 4,925,966 | 5/1990 | Kobayashi et al. |
| 4,990,661 | 2/1991 | Petersen et al. |
| 5,021,605 | 6/1991 | Kobayashi et al. |
| 5,051,418 | 9/1991 | Schriewer et al. |
| 5,068,411 | * 11/1991 | Kobayashi et al. |
| 5,190,955 | 3/1993 | Schriewer et al. |

FOREIGN PATENT DOCUMENTS

| | | |
|---|---|---|
| CA | 1255330 | 6/1989 |
| WO | 97/31001 | 8/1997 |
| WO | 98/26768 | 6/1998 |

* cited by examiner

Primary Examiner—Paul J. Killos

(57) ABSTRACT

The present invention relates to a process for preparing 3-cyano-2,4-dihalogeno-5-fluoro-benzoic acid, to intermediates for carrying out the process and to processes for preparing these intermediates.

5 Claims, No Drawings

METHOD FOR PREPARING 3-CYANO-2,4-DIHALOGENO-5-FLUORO-BENZOIC ACID

The present invention relates to a process for preparing 3-cyano-2,4-dihalogeno-5-fluoro-benzoic acids, to intermediates for carrying out the process and to processes for preparing these intermediates.

3-Cyano-2,4-dichloro-5-fluoro-benzoic acid is known from DE-A-3 702 393. It is prepared from 3-amino-2,4-dichloro-5-fluoro-benzoic acid by diazotization and reaction of the diazonium salt with cyanide salts. This process is unfavourable, in particular when it is carried out on a relatively large scale.

The present invention provides

1. Process for preparing 3-cyano-2,4-dihalogeno-5-fluorobenzoic acids of the formula (I)

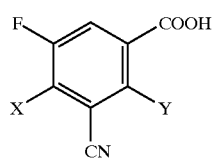

(I)

in which

X and Y independently of one another each represent halogen by hydrolytic cleavage of a) 3-cyano-2,4-dihalogeno-5-fluorobenzamides of the formula (II)

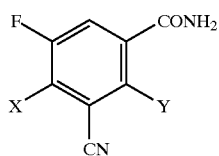

(II)

in which
X and Y independently of one another each represent halogen, or b) 1,3-dicyano-2,4-dihalogeno-5-fluorobenzenes of the formula (III)

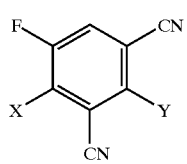

(III)

in which
X and Y independently of one another each represent halogen, or c) 3-cyano-2,4-dihalogeno-5-fluorobenzoic esters of the formula (IV)

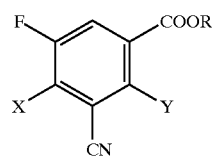

(IV)

in which
X and Y independently of one another each represent halogen and
R represents $C_{1-4}$-alkyl which may optionally be substituted.

2. The novel compounds of the formulae (II)

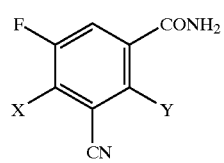

(II)

and (IV)

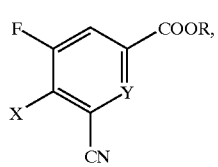

(IV)

in which
X and Y independently of one another each represent halogen and
R represents $C_{1-4}$-alkyl which may optionally be substituted,
except for methyl3-cyano-2,4,5-trifluorobenzoate.

3. Process for preparing 3-cyano-2,4-dihalogeno-5-fluoro-benzamides of the formula (II)

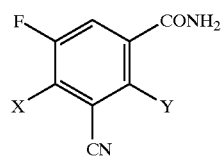

(II)

or esters of the formula (IV)

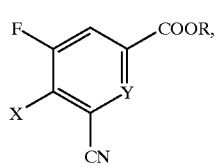

(IV)

characterized in that 1,3-dicyano-2,4-dihalogeno-5-fluorobenzenes of the formula (III)

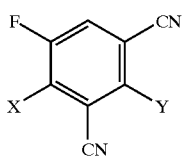

in which

X and Y are each as defined above, are hydrolyzed in the presence of water or in the presence of alcohols.

4. The novel compounds of the formula (III)

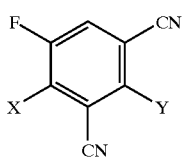

in which

X and Y represent different radicals from the group consisting of fluorine and chlorine, or both radicals represent chlorine.

5. Process for preparing the compounds of the formula (III)

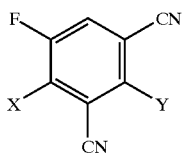

in which

X and Y represent different radicals from the group consisting of fluorine and chlorine, characterized in that 1,2,4-trifluoro-3,5-dicyanobenzene (2,4,5-trifluoro-isophthalonitrile) is reacted with a metal halide.

1,2,4-Trifluoro-3,5-dicyanobenzene and its preparation are known from EP-A-307 897.

In the above formulae, X and Y each preferably represent fluorine or chlorine. In the compounds of the formulae (II) and (IV), they particularly preferably represent identical radicals fluorine or chlorine.

Among the compounds of the formula (III), particular preference is given to 2,4-dichloro-5-fluoroisophthalonitrile.

R preferably represents methyl, ethyl, propyl or benzyl.

If 3-cyano-2,4,5-trifluorobenzamide is used as starting material in the process a) for preparing 3-cyano-2,4,5-trifluorobenzoic acid, the reaction can be illustrated by the following formula scheme:

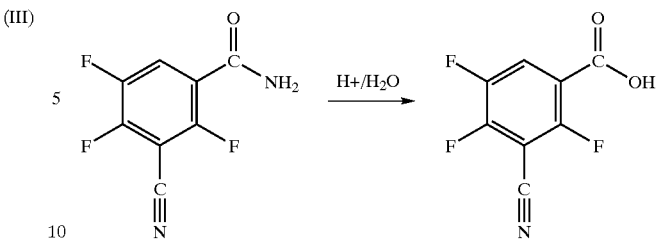

The amides of the formula (II) used as starting materials are novel. Their preparation is described further below.

The hydrolysis is carried out in the presence of acids and water. Suitable for use as acids are organic and inorganic strong acids. Examples which may be mentioned are HCl, HBr, sulphuric acid, methanesulphonic acid, trifluoromethanesulphonic acid, benzenesulphonic acid, toluenesulphonic acid and strongly acidic ion exchangers in the presence of water.

The solvent used can be an excess of the acid used as reagent, or an organic solvent. Suitable organic solvents are acids, such as formic acid, acetic acid, propionic acid, ethers, such as dimethoxyethane, dioxane, ketones, such as acetone, butanone.

The reaction components may be added in any order. The mixture is subsequently heated to the required temperature.

The reaction temperature is in the range from 0 to 200° C., preferably from 20 to 150° C.

The reaction can be carried out under atmospheric pressure or under a pressure of from 0 to 50 bar, preferably from 0 to 6 bar.

The products are filtered off from the reaction mixture, if appropriate after dilution with water. If a large excess of acid or a solvent is used, it may be advantageous to carry out a distillation and to isolate the product by extraction.

If 4-chloro-2,5-difluoro-isophthalonitrile is used as starting material for preparing 4-chloro-2,5-difluoro-3-cyanobenzoic acid according to process 1b), the reaction can be illustrated by the reaction scheme below:

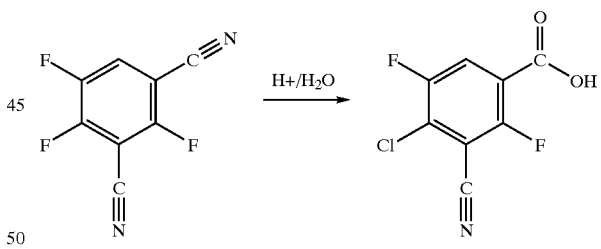

2,4,5-Trifluoro-isophthalonitrile is known from the literature (EP-A-307 897). 2,4-Dichloro-5-fluoro-isophthalonitrile is novel. Its preparation is described further below.

The hydrolysis with acids is carried out in the presence of water. Suitable for use as acids are organic and inorganic strong acids. Examples which may be mentioned are HCl, HBr, sulphuric acid, methanesulphonic acid, trifluoromethanesulphonic acid, benzenesulphonic acid, toluenesulphonic acid and strongly acidic ion exchangers in the presence of water.

The solvent used can be an excess of the acid used as reagent, or an organic solvent. Suitable organic solvents are acids, such as formic acid, acetic acid, propionic acid, ethers, such as dimethoxyethane, dioxane, ketones, such as acetone, butanone.

The reaction components may be added in any order. The mixture is subsequently heated to the required temperature.

The reaction temperature is in the range from 0 to 200° C., preferably from 20 to 150° C.

The reaction can be carried out under atmospheric pressure or under a pressure of from 0 to 50 bar, preferably from 0 to 6 bar.

The products are filtered off from the reaction mixture, if appropriate after dilution with water. If a large excess of acid or a solvent is used, it may be advantageous to carry out a distillation and to isolate the product by extraction.

If methyl 3-cyano-2,4,5-trifluoro-benzoate is used as starting material in the process 1c) for preparing 3-cyano-2,4,5-trifluorobenzoic acid, the reaction can be illustrated by the formula scheme below:

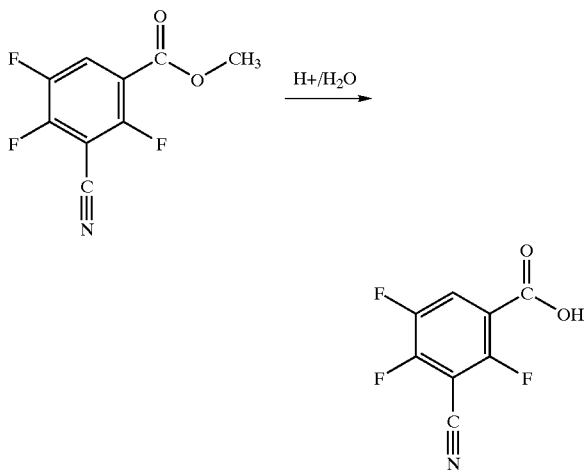

The esters of the formula (IV) used as starting materials are novel. Their preparation is described further below.

The hydrolysis is carried out in the presence of acids and water. Suitable for use as acids are organic and inorganic strong acids. Examples which may be mentioned are HCl, HBr, sulphuric acid, methanesulphonic acid, trifluoromethanesulphonic acid, benzenesulphonic acid, toluenesulphonic acid and strongly acidic ion exchangers in the presence of water.

The solvent used can be an excess of the acid used as reagent, or an organic solvent. Suitable organic solvents are acids, such as formic acid, acetic acid, propionic acid, ethers, such as dimethoxyethane, dioxane, ketones, such as acetone, butanone.

The reaction components may be added in any order. The mixture is subsequently heated to the required temperature.

The reaction temperature is in the range from 0 to 200° C., preferably from 20 to 150° C.

The reaction can be carried out under atmospheric pressure or under a pressure of from 0 to 50 bar, preferably from 0 to 6 bar.

The products are extracted from the reaction mixture, if appropriate after dilution with water. If a large excess of acid or a solvent is used, it may be advantageous to carry out a distillation.

As already mentioned, the compounds of the formula (IV) are novel.

If 2,4-dichloro-5-fluoro-isophthalonitrile is used as starting material for their preparation according to process 3), the reaction can be represented by the formula scheme below:

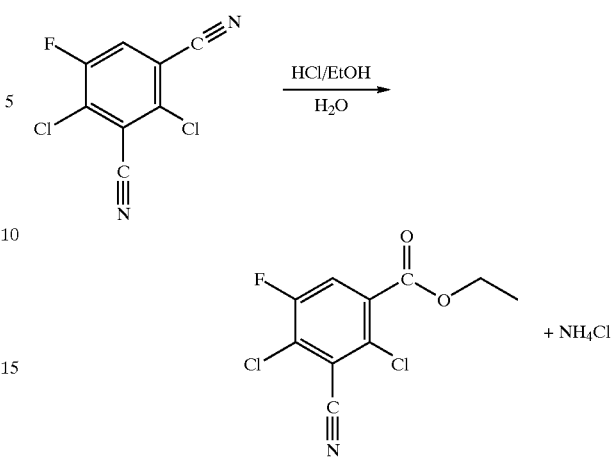

The reaction proceeds via the iminoester intermediate and its hydrolysis with water. The formation of the corresponding amide is observed as a side reaction. If no water is added, the amide formation becomes the predominant reaction (see below).

2,4,5-Trifluoro-isophthalonitrile is known from the literature (EP-A-307 897). 2,4-Dichloro-5-fluoro-isophthalonitrile is novel, its preparation is described further below.

The compound of the formula (II) is prepared by hydrolysis of the corresponding dinitriles with acids in the presence of water and alcohols.

The reaction is carried out in the presence of from 1 to 10 equivalents of water and primary and secondary aliphatic alcohols. Preference is given to methanol, ethanol, propanol and butanol. Acids used can be organic and inorganic strong acids, such as HCl, HBr, sulphuric acid, methanesulphonic acid, trifluoromethanesulphonic acid, benzenesulphonic acid, toluenesulphonic acid and strongly acidic ion exchangers.

In addition to from I to 10 mol of alcohol, it is also possible to employ from 1 to 10 mol of water per mole of dinitrile.

The reaction can be carried out in the presence or absence of solvent. The solvent used can be an excess of the alcohol used as reagent, or an inert organic solvent. Suitable inert solvents are: all inert organic solvents, such as hydrocarbons, for example pentane, hexane, heptane, petroleum ether, benzine, ligroine, benzene, toluene; halogenated hydrocarbons, for example dichloromethane, chloroform, chlorobenzene, dichlorobenzene, trichloroethane; ethers, for example diethyl ether, dipropyl ether, dibutyl ether, ethylene glycol dimethyl ether, diethylene glycol diethyl ether.

Dintrile and alcohol are initially charged and acid is added, and the water is then added. However, it is also possible to initially charge the water required for the reaction directly.

The reaction temperature is in the range from −20 to 150° C. Preference is given to temperatures from 10 to 100° C.

The reaction can be carried out at atmospheric pressure or elevated pressure of from 0 to 50 bar. Preference is given to a pressure from 0 to 6 bar.

The reaction mixture is diluted with water and extracted. If a large excess of alcohol or an inert solvent were used, the solvent can be distilled off first. Any amide formed as reaction by-product can be separated off.

As already mentioned, the compounds of the formula (II) are novel.

If 2,4,5-trifluoro-isophthalonitrile is used as starting material for their preparation according to process 3), the reaction can be represented by the formula scheme below:

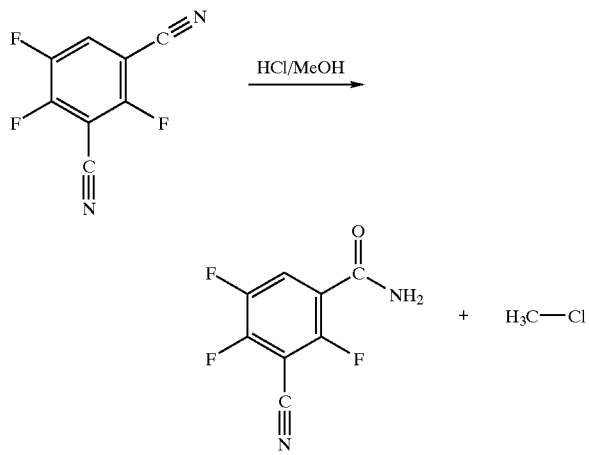

The reaction proceeds via the intermediate imino esters, from which the amides are formed by elimination of the alkyl radical.

2,4,5-Trifluoro-isophthalonitrile is known from the literature (EP-A-307 897). 2,4-Dichloro-5-fluoro-isophthalonitrile is novel, the preparation is described further below.

The reaction is carried out with primary or secondary aliphatic alcohols in the presence of acids. Preference is given to methanol, ethanol, propanol and butanol. Particular preference is given to methanol. Suitable for use as acids are organic and inorganic strong acids, such as HCl, HBr.

From 1 to 10 mol of alcohol can be used per mole of dinitrile.

The reaction can be carried out in the presence or absence of solvent. The solvent used can be an excess of the alcohol used as reagent, or an inert organic solvent. Suitable inert solvents are: all inert organic solvents, such as hydrocarbons, for example pentane, hexane, heptane, petroleum ether, benzine, ligroine, benzene, toluene; halogenated hydrocarbons, for example dichloromethane, chloroform, chlorobenzene, dichlorobenzene, trichloroethane; ethers, for example diethyl ether, dipropyl ether, dibutyl ether, ethylene glycol dimethyl ether, diethylene glycol diethyl ether.

Dinitrile and alcohol are initially charged, and acid is added.

The reaction temperature is in the range from –20 to 150° C. Preference is given to temperatures from –0° to 100° C.

The reaction can be carried out at atmospheric pressure or an elevated pressure of from 0 to 50 bar. Preference is given to a pressure from 0 to 6 bar.

The products are filtered off from the reaction mixture, if appropriate after dilution with water. If a large excess of alcohol or an inert solvent was used, this can be preceded by distillation.

Compounds of the formula (III) in which X and Y do not simultaneously represent F are novel. Starting from 2,4,5-trifluoro-isophthalonitrile, their preparation according to process 5) can be represented by the formula scheme below:

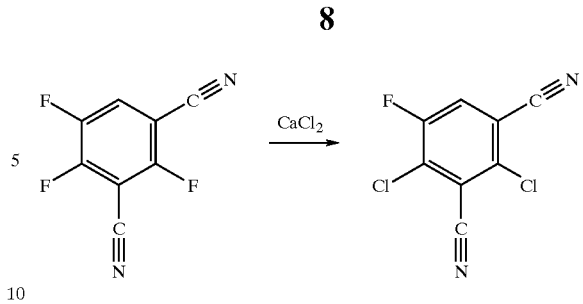

2,4,5-Trifluoro-isophthalonitrile is known from the literature (EP-A-307 897).

The halogen exchange is carried out by reaction with inorganic chloride salts.

Suitable for use as inorganic chloride salts are $MgCl_2$ and $CaCl_2$. It is also possible to catalyse the reaction, for example using tetraalkylammonium salts, crown ethers, etc.

From 0.5 to 10 mol of inorganic salt are employed per fluorine to be exchanged. Preference is given to from 0.5 to 2 mol.

The reaction can be carried out in the presence or absence of solvent. Suitable solvents are all inert organic solvents, for example pentane, hexane, heptane, petroleum ether, benzine, ligroine, benzene, toluene, dichloromethane, chloroform, chlorobenzene, dichlorobenzene, trichloroethane, ethers, such as dibutyl ether, ethylene glycol dimethyl ether, diethylene glycol diethyl ether, ketones, such as acetone, methyl ethyl ketone, cyclohexanone, and also N-methylpyrrolidinone, dimethyl sulphone, sulpholane.

The substances are mixed and heated to the required temperature. The order of addition is immaterial. Depending on how the reaction is carried out, it is possible to exchange one or two fluorine atoms for chlorine.

The reaction temperature is in the range from 50 to 350° C. Preference is given to temperatures from 90 to 250° C.

The reaction can be carried out under atmospheric or elevated pressure. If low-boiling solvents are used, it may be favourable to carry out the reaction under elevated pressure. Pressure range: a superatmospheric pressure of from 0 to 100 bar. Preferably: from 0 to 50 bar.

The products are isolated by filtering off the inorganic salts and subjecting the filtrate to fractional distillation. If a water-miscible solvent was employed, it is also possible to pour the mixture into water and extract the product.

3-Cyano-2,4-dihalogeno-5-fluoro-benzoic acid can be used, for example, for preparing the following compounds (VIII) known from U.S. Pat. No. 4,990,517:

7-chloro-8-cyano-1-cyclopropyl-6-fluoro-1,4-dihydro-4-oxo-3-quinolinecarboxylic acid,
methyl7-chloro-8-cyano-1-cyclopropyl-6-fluoro- 1,4-dihydro-4-oxo-3-quinolinecarboxylate,
8-cyano-1-cyclopropyl-6,7-difluoro-1,4-dihydro-4-oxo-3-quinolinecarboxylic acid, ethyl 8-cyano-1 -cyclopropyl-6,7-difluoro- 1,4-dihydro-4-oxo-3-quinolinecarboxylate.

To this end, for example, 3-cyano-2,4,5-trifluorobenzoic acid is reacted in the form of its acid chloride with the β-dimethylamino-acrylic acid ester of the formula (V), and the resulting product of the formula (VI) is further reacted with cyclopropylamine to give a compound of the formula (VII), and the abovementioned compound (VII) is subsequently obtained:

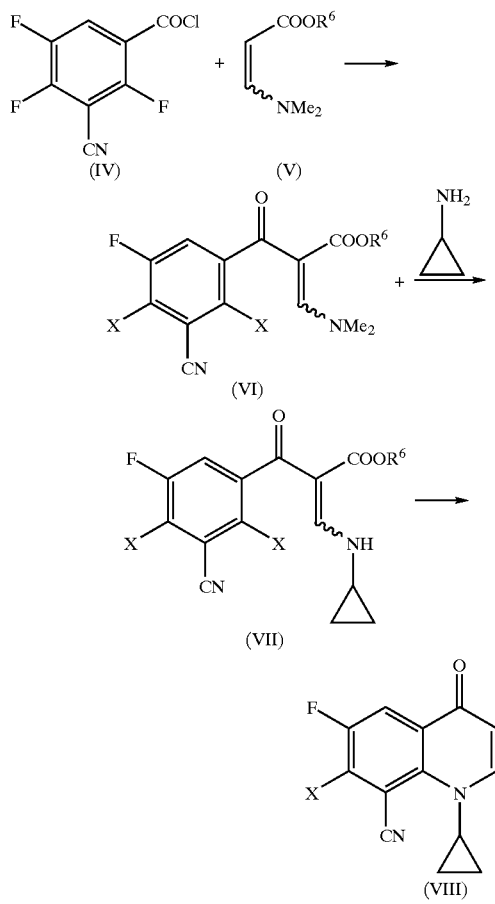

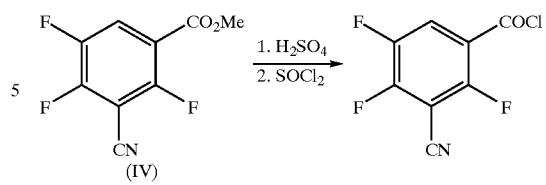

From the compounds of the formula (VIII), antibacterially active compounds can be prepared by reaction with suitable amines.

If, for example, 7-chloro-8-cyano-1-cyclopropyl-6-fluoro-1,4-dihydro-4-oxo-3-quinolinecarboxylic acid and 2,8-diazabicyclo[4.3.0]nonane are reacted, the course of the reaction can be represented by the formula scheme below:

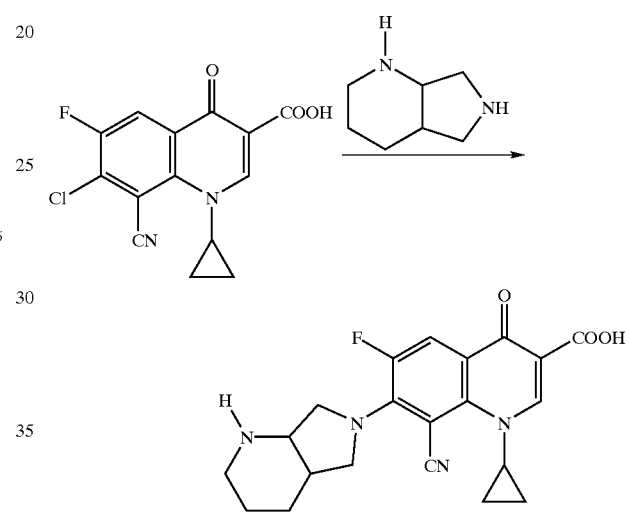

The preparation of these compounds is described in DE-A-196 33 805 of the applicant, which is not a prior art document.

The examples below illustrate the present invention without limiting its scope.

In the formula scheme above

X represents halogen, in particular fluorine or chlorine, $R^6$ represents $C_{1-4}$-alkyl, in particular methyl or ethyl.

It is also possible to react a compound of the formula (IV) directly with β-cyclopropylamino-acrylic acid ester:

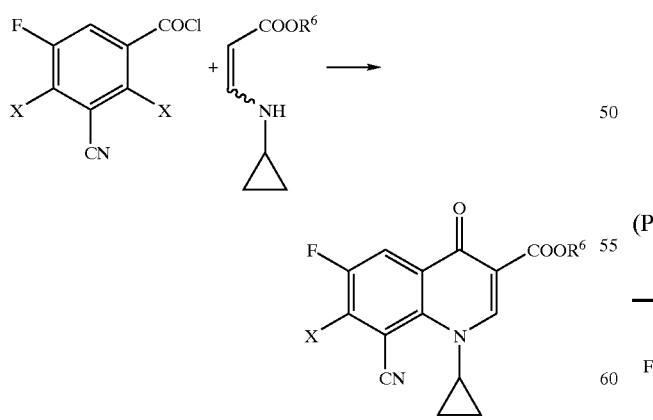

(In the formulae, X and $R^6$ -are each as defined above.)

The acid chloride of 3-cyano-2,4,5-trifluorobenzoic acid can be prepared from the esters of the formula (IV) according to the following scheme:

EXAMPLE 1

(Process 1a)

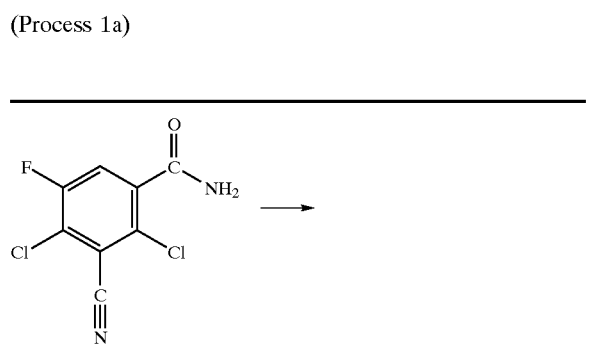

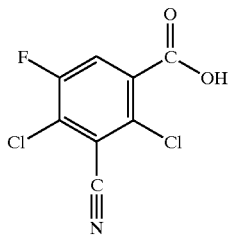

| Amount | Mol | Text |
|---|---|---|
| 0.4 g | 1.72 m | of 3-cyano-2,4-dichloro-5-fluoro-benzamide and |
| 5 ml | | of concentrated hydrochloric acid were heated under reflux for three hours. The mixture was then concentrated and the residue was dried over sulphuric acid in a dessicator.<br>Yield: 370 mg<br>Purity: 84% (HPLC area) 3-cyano-2,4-dichloro-5-fluoro-benzoic acid<br>12% (HPLC area) 3-cyano-2,4-dichloro-5-fluoro-benzamide (starting material) |

EXAMPLE 2

(Process 1b)

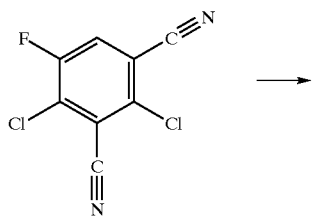

| Amount | Mol | Text |
|---|---|---|
| 2.5 g | 12 m | of 2,4-dichloro-5-fluoro-isophthalonitrile were suspended in |
| 25 ml | | of methanol, and the mixture was cooled to 0° C. and saturated with gaseous hydrochloric acid. The reaction mixture was allowed to stand at −16° C. for 60 hours and was then concentrated. The residue was admixed with |
| 38 ml | | of concentrated hydrochloric acid and heated at reflux for three hours. The mixture was then poured into |
| 120 ml | | of water, and the precipitate was filtered off with suction and dried over sulphuric acid in a dessicator.<br>Yield: 1.86 g Purity:<br>87% of 3-cyano-2,4-dichloro-5-fluoro-benzoic acid<br>10% of 3-cyano-2,4-dichloro-5-fluoro-benzamide |

EXAMPLE 3

(Process 1b)

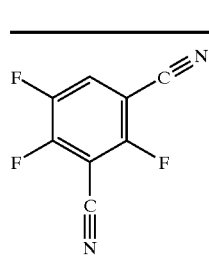

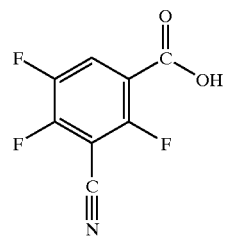

| Amount | Mol | Text |
|---|---|---|
| 1 g | 5.5 m | of 2,4,5-trifluoro-isophthalonitrile, |
| 6.3 ml | | of water, |
| 6.3 ml | | of glacial acetic acid and |
| 0.63 ml | | of 96% strength sulphuric acid were heated at reflux for 24 hours. The mixture was then poured into |
| 50 ml | | of water and admixed with |
| 25 ml | | of dichloromethane. The aqueous phase was then adjusted to pH 9 using 45% strength NaOH, and the organic phase was then separated off and re-extracted twice with dichloromethane. The extracts were discarded. The aqueous phase that remained was then adjusted to pH 2 using concentrated hydrochloric acid and extracted three times altogether with in each case |
| 25 ml | | of dichloromethane. The combined extracts were dried using sodium sulphate and concentrated.<br>Residue: 470 mg<br>Purity: 80% (GC/MS area) |

EXAMPLE 4

(Process 1c)

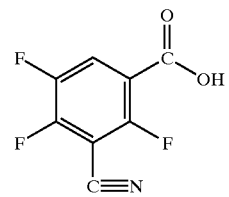

| Amount | Mol | Text |
|---|---|---|
| 2 g | 8.7 m | of ethyl 3-cyano-2,4,5-trifluoro-benzoate (purity 79%), |
| 10 ml | | of glacial acetic acid, |
| 10 ml | | of water and |
| 1 ml | | of 96% strength sulphuric acid are heated at reflux for 7.5 hours. The mixture is then cooled, poured into |
| 100 ml | | of water and extracted three times with dichloromethane. The extract is admixed with |
| 100 ml | | of water and the PH of the aqueous phase is adjusted to 8.5 with stirring. The organic phase is separated off, and the aqueous phase is re-extracted with dichloromethane. The organic extracts are discarded. |

EXAMPLE 5

(Process 3)

| Amount | Mol | Text |
|---|---|---|
| 50 ml | | of dichloromethane are then added to the aqueous phase, and the mixture is acidified using sulphuric acid. The dichloromethane is separated off and the mixture is re-extracted with dichloromethane. The combined extracts are then dried using $Na_2SO_4$ and concentrated. The residue is dried over KOH in a dessicator. Yield: 1.2 g (81% of theory) Purity: 95% (HPLC area) Melting point: 146° C. |

EXAMPLE 5

(Process 3)

| Amount | Mol | Text |
|---|---|---|
| 9 g | 42 m | of 2,4-dichloro-5-fluoro-isophthalonitrile were suspended in |
| 90 ml | | of methanol, the mixture was cooled to 5° C. and gaseous hydrochloric acid was introduced until the mixture was saturated. The resulting solution was stirred at room temperature for 24 hours. The solution was then concentrated and the residue was stirred with dichloromethane and filtered off with suction. Yield: 8.04 g Purity: 95% (HPLC area) Melting point: 178° C. |

EXAMPLE 6

(Process 3)

| Amount | Mol | Text |
|---|---|---|
| 5.52 g | 30 m | of 2,4,5-trifluoro-isophthalonitrile (purity 86%) are initially charged in |
| 60 ml | | of dry ethanol, and gaseous hydrochloric acid is introduced with ice-cooling until the mixture is saturated. The mixture is stirred at room temperature for four hours, then |
| 4.8 ml | 0.266 m | of water are added and the mixture is heated at reflux for four hours. The mixture is then concentrated and the residue is partitioned between water and chloroform. The organic phase is separated off and the aqueous phase is re-extracted twice with chloroform. The combined extracts are dried using $Na_2SO_4$ and concentrated. The residue is distilled using a kugelrohr. Boiling point: 220° C. (42 mbar) Yield: 4.21 g (55% of theory) Purity: 79% (HPLC area) $^1$H NMR ($CDCl_3$): 8.1 ppm (m, 1H, Ar—H) 4.4 ppm (q, J = 8 Hz, 2H, —$OCH_2$—) 1.4 ppm (t, J = 8 Hz, 3H, —$CH_3$) |

EXAMPLE 7

(Process 3)

| Amount | Mol | Text |
|---|---|---|
| 0.5 g | 2.3 m | of 2,4-dichloro-5-fluoro-isophthalonitrile was dissolved in |
| 10 ml | | of methanol and, with efficient cooling at 0° C., the mixture was saturated with gaseous HCl. The mixture was subsequently allowed to stand at -10° C. for 72 hours. |

-continued

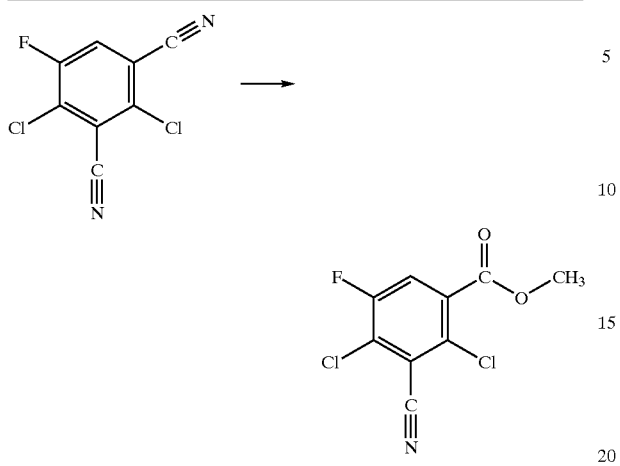

| Amount | Mol | Text |
|---|---|---|
| 1 ml | | of 96% pure aqueous methanol was then added, and the mixture was heated under reflux for three hours. The mixture was subsequently concentrated under reduced pressure, the residue was partitioned between chloroform and saturated bicarbonate solution and the organic phase was separated off, dried with sodium sulphate and concentrated.<br>Residue: 410 mg<br>According to HPLC, this contains<br>10% of starting material<br>7.5% of amide<br>76% of methyl ester. |

EXAMPLE 8
(Process 5)

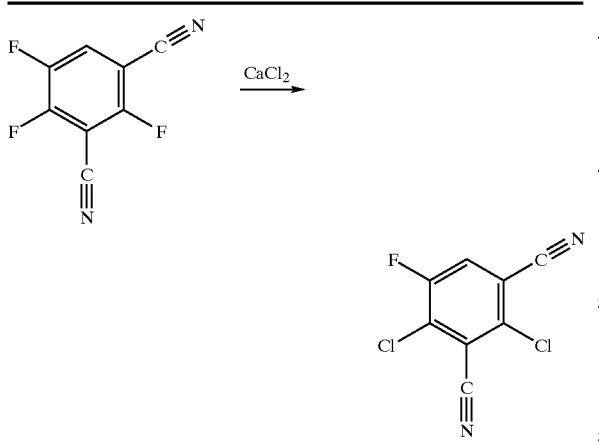

| Amount | Mol | Text |
|---|---|---|
| 13.5 g | 74 m | of 2,4,5-trifluoro-isophthalonitrile, |
| 125 ml | | of sulpholane and |
| 17.7 g | | of freshly powdered calcium chloride are heated at 200° C. for 24 hours. The mixture is subsequently poured into |
| 1200 ml | | of water. The fine precipitate is filtered off with suction and dried.<br>Yield: 13.8 g<br>For purification, the product can be filtered through silica gel using toluene/hexane.<br>Yield: 12.8 g |

-continued

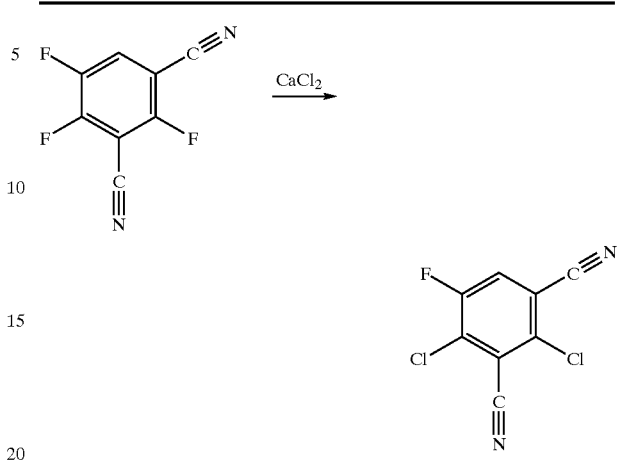

| Amount | Mol | Text |
|---|---|---|
| | | Purity: 96% HPLC area<br>Melting point: 119° C. |

EXAMPLE 9
(Process 5)

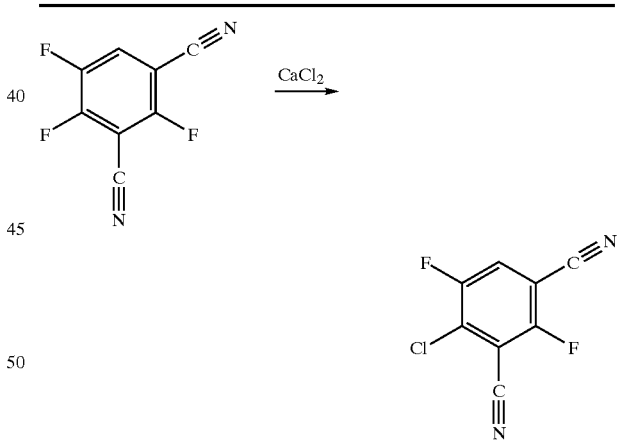

| Amount | Mol | Text |
|---|---|---|
| 0.55 g | 3 m | of 2,4,5-trifluoro-isophthalonitrile, |
| 5 ml | | of sulpholane and |
| 0.37 g | 3.3 m | of freshly powdered calcium chloride were heated at 200° C. for 1.5 hours. The mixture was subsequently poured into |
| 100 ml | | of water and extracted twice with ether. The extract was dried using sodium sulphate and concentrated.<br>Yield: 0.56 g<br>Composition: 75% of 4-chloro-2,5-difluoro-isophthalonitrile<br>25% of 5-fluoro-2,4-dichloro-isophthalonitrile (HPLC area) |

What is claimed is:

1. Process for preparing 3-cyano-2,4-dihalogeno-5-fluorobenzoic acids of the formula (I)

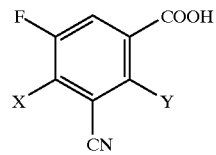

(I)

in which

X and Y independently of one another each represent halogen by hydrolytic cleavage of a) 3-cyano-2,4-dihalogeno-5-fluorobenzamides of the formula (II)

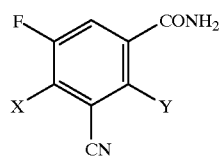

(II)

in which

X and Y independently of one another each represent halogen, or b) 1,3-dicyano-2,4-dihalogeno-5-fluorobenzenes of the formula (III)

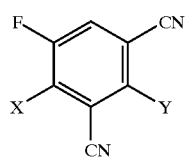

(III)

in which

X and Y independently of one another each represent halogen, or c) 3-cyano-2,4-dihalogeno-5-fluorobenzoic esters of the formula (IV)

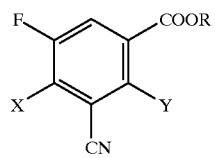

(IV)

in which

X and Y independently of one another each represent halogen and

R represents $C_{1-4}$-alkyl which may optionally be substituted.

2. Compounds of the formulae (II)

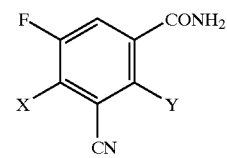

(II)

and (IV)

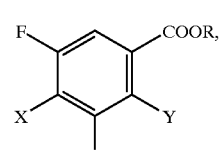

(IV)

in which

X and Y independently of one another each represent halogen and

R represents $C_{1-4}$-alkyl which is optionally substituted, except for methyl 3-cyano-2,4,5-trifluorobenzoate.

3. Process for preparing 3-cyano-2,4-dihalogeno-5-fluoro-benzamides of the formula (II)

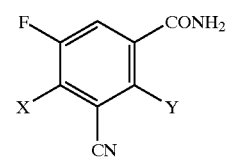

(II)

or esters of the formula (IV)

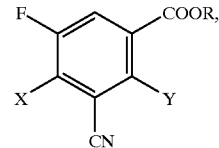

(IV)

in which

X and Y independently of one another each represent halogen and

R represents $C_{1-4}$-alkyl which is optionally substituted, characterized in that 1,3-dicyano-2,4-dihalogeno-5-fluorobenzenes of the formula (III)

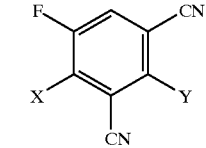

(III)

in which

X and Y are each as defined above, are hydrolyzed in the presence of water or in the presence of alcohols.

4. The novel compounds of the formula (III)

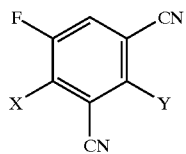
(III)

in which

X and Y represent different radicals from the group consisting of fluorine and chlorine, or both radicals represent chlorine.

5. Process for preparing the compounds of the formula (III)

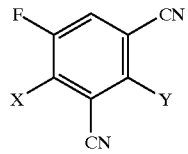
(III)

in which

X and Y represent different radicals from the group consisting of fluorine and chlorine, characterized in that 1,2,4-trifluoro-3,5-dicyanobenzene (2,4,5-trifluoro-isophthalonitrile) is reacted with a metal halide.

* * * * *